United States Patent [19]

Zanger

[11] Patent Number: 5,268,624
[45] Date of Patent: Dec. 7, 1993

[54] FOOT PEDAL CONTROL WITH USER-SELECTABLE OPERATIONAL RANGES

[75] Inventor: Frank Zanger, Hayward, Calif.
[73] Assignee: Allergan, Inc., Irvine, Calif.
[21] Appl. No.: 961,138
[22] Filed: Oct. 14, 1992
[51] Int. Cl.$^5$ .............................................. H01H 3/14
[52] U.S. Cl. .................................. 318/551; 604/65
[58] Field of Search .............. 318/551, 567, 569, 590, 318/591, 600, 685; 604/65

[56] References Cited
U.S. PATENT DOCUMENTS

| | | | |
|---|---|---|---|
| 4,933,843 | 6/1990 | Scheller et al. | 364/413.01 |
| 4,983,901 | 1/1991 | Lehmer | 318/685 |
| 5,091,656 | 2/1992 | Gahn | 307/119 |

Primary Examiner—Bentsu Ro
Attorney, Agent, or Firm—Walter A. Hackler

[57] ABSTRACT

A method is provided for the operation of phacoemulsifier apparatus in the performance of a phacoemulsification in which three modes of operation are required. The method for the establishment of an angular range of foot pedal operation to each of the modes of the operation and assigning a linear relationship between the angular position of the foot pedal within the range and an output signal from the foot pedal within each range. The foot pedal control sensitivity is obtained by adjusting the range of position of the foot pedal within each of the selected modes.

4 Claims, 1 Drawing Sheet

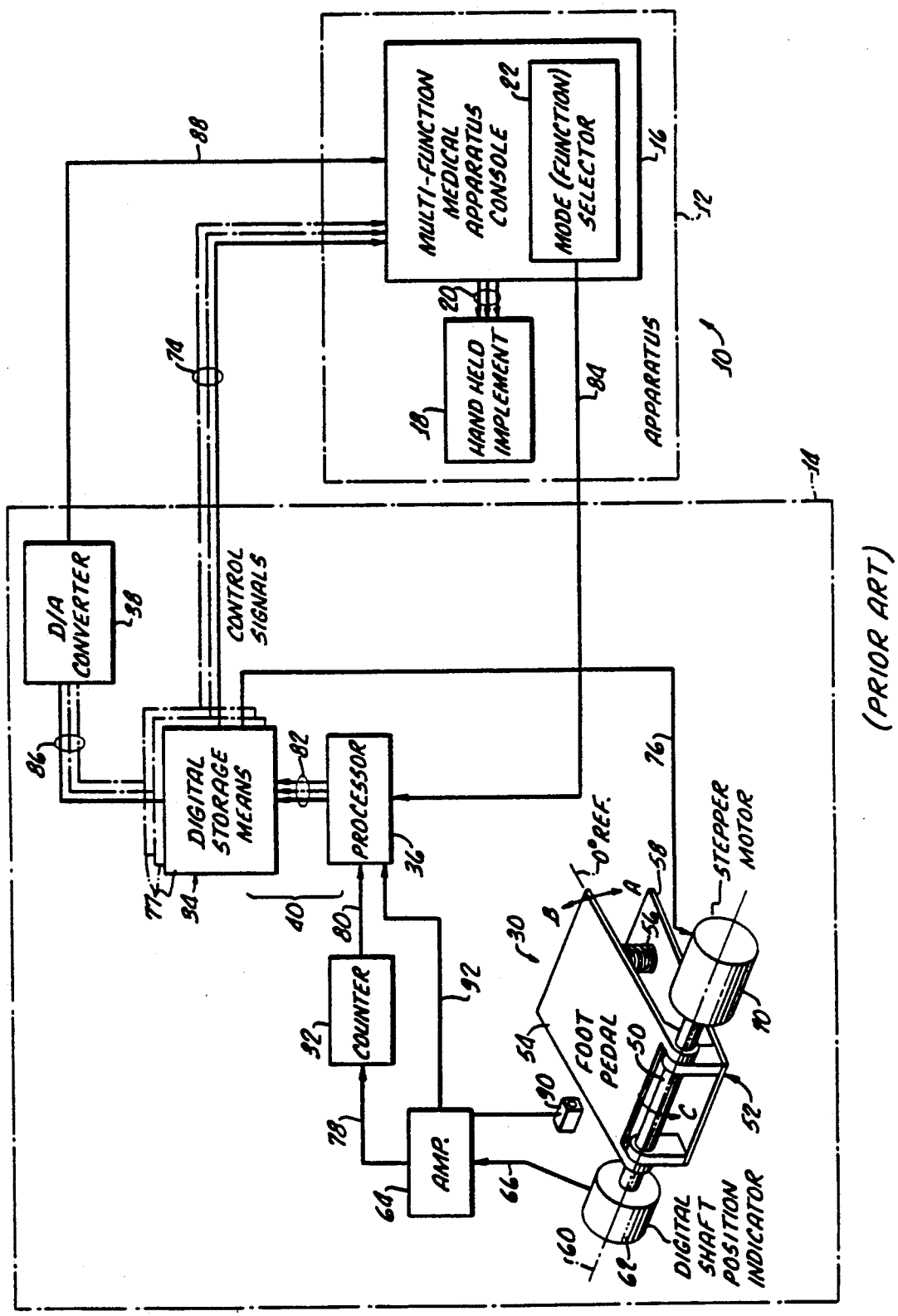

FOOT PEDAL CONTROL WITH USER-SELECTABLE OPERATIONAL RANGES

The present invention generally relates to medical devices and more particularly relates to the operation of foot pedal controls for phacoemulsifier apparatus.

Phacoemulsifier apparatus is utilized for surgically removing the natural, crystalline lens cataract eyes in preparation for the insertion of an artificial intraocular lens. Typically, such apparatus includes a hand-held surgical implement including a needle which is inserted into a patient's eye in order to remove cataractous matter therein.

The phacoemulsifier hand-held surgical implement operates in a number of modes, which include irrigating the eye, ultrasonically emulsifying the eye lens, and aspirating the emulsified lens from the eye (phacoemulsification) as discussed in U.S. Pat. No. 4,983,901. Problems arise in providing adequate control of the device through its various functions or modes, and these difficulties have led to the development of foot pedal controls.

Improved foot pedal control systems, such as that described in U.S. Pat. No. 4,983,901, provide for a virtually unlimited number of control variations and modes for operating phacoemulsifier apparatus. While this device offers a substantial improvement in the art for prior foot pedal controls, a specific operational routine has yet to be developed for enhancing and applying the available technology on a practical basis for physician use.

A physician's demands on phacoemulsifier apparatus are dependent, in part, on the experience of the physician in using the device. A programmable control system, such as that set forth in U.S. Pat. No. 4,983,901, is advantageous; however, specific use of the system in enabling both experienced and inexperienced physicians to effectively utilize the device is not apparent from the device itself nor derivable therefrom.

The present invention provides a method for operating a phacoemulsifier through a foot pedal that is "configured" to one or more end users, depending upon the experience thereof. This enables transitioning surgeons to become more comfortable with the procedure and have fewer concerns about the restrictions of the equipment during a phacoemulsification.

SUMMARY OF THE INVENTION

In accordance with the present invention, a method useful in performance of phacoemulsification for operating a phacoemulsifier apparatus enables the adjustment of various operating modes of the apparatus. The apparatus suitable for the method of the present invention includes at least three modes of operation, namely: irrigation of an eye with a saline solution; simultaneous irrigation and aspiration of fluid; and simultaneous irrigation, emulsification of tissue, and aspiration of same with set modes being controlled through a foot pedal.

More specifically, the method in accordance with the present invention includes establishing an angular range of foot pedal operation for each of the modes of operation, with the angular ranges being consecutive and, in combination, defining a total angular displacement for the foot pedal. A linear relation surface is assigned between the angular position of the foot pedal within each range and an output signal from the foot pedal within each range. Importantly, the method includes adjusting the foot pedal control sensitivity by changing the range of position of the foot pedal within selected modes.

In still greater detail, the total angular displacement for the foot pedal may be established at 15°; the foot pedal angular range for the irrigation mode may be set at 2°, while the angular foot pedal range for the irrigation mode and the simultaneous irrigation and aspiration mode may be set between about 5° and 8°.

BRIEF DESCRIPTION OF THE DRAWING

The advantages and features of the present invention will be better understood by the following detailed description when considered in conjunction with the accompanying drawing of a prior art foot control device.

DETAILED DESCRIPTION

The drawing shows a prior art medical equipment system 10 suitable for use in the present invention. A complete description of this device may be found in U.S. Pat. No. 4,983,901 which is incorporated herein in toto. The prior art system 10 generally comprises a medical apparatus 12 having operatively connected thereto a digital electronic foot control system 14 in accordance with the present invention. Medical apparatus 12 is a multi-function medical phacoemulsifier. Forming medical apparatus 14 are an equipment console or cabinet 16 and an associated hand-held medical implement or tool 18 which is operably connected to the console by an umbilical 20 typically several feet in length.

Console 16 is preferably constructed for housing all of the equipment necessary for enabling the functioning of medical apparatus 12 in a prescribed manner through hand-held implement 18. The console 16 may, for example, include a power supply, a vacuum pump, a source of ultrasonic power, a fluid irrigation pump, a source of irrigating fluid, and various other hardware and electronic circuits, none of which are shown as they do not form any part of the present invention.

The medical apparatus 14 is a multi-function apparatus, and console 16 includes a manually-operated function or mode selector 22 through which the various operational functions or modes of operation are selected. As mentioned above, the functions of a phacoemulsifier include irrigation, lens emulsification, irrigation and aspiration, cauterization and phacoemulsification.

Generally comprising foot pedal control system 14, to which the present invention is directed, and as is depicted in the drawing and more particularly described below, are foot pedal means or assembly 30, a digital counter 32, digital storage means 34, data processor means 36, and digital to analog (D/A) converter 38. Together, digital storage means 34 and data processor means 36 can be considered to form a logic means 40.

Foot pedal assembly 30 comprises a pedal shaft 50 which is rotationally mounted in a pedal housing or mount 52, only part of which is shown in the drawing. Non-rotatably fixed to central regions of pedal shaft 50 is a foot pedal 54 which is biased or urged, for example, by a spring or springs 56, to a zero rotational reference position (that is, the undepressed position).

In operation, foot pedal 54 is depressed by an operator's foot downwardly (direction of Arrow A) toward a housing base plate 58, spring 56, when foot pressure on pedal 54 is released, returning the pedal (in the direction of Arrow B) to the zero reference position.

Non-rotatably connected to one end region of pedal shaft 50, on a shaft rotational axis 60, is a bidirectional digital rotational position detector or shaft encoder 62, which may be of a known type. Shaft encoder 62 may be connected to pedal shaft 50 through a drive, for example, a 5:1 speed-up drive (as described below).

As pedal 54 is depressed from the zero reference position, digital position detector 62 provides a digital signal to an amplifier 64, over a conduit 66, the digital signal containing data relative to the rotational motion of pedal shaft 50 relative to the zero reference position. Detector 62 may, for example, be configured for providing a series of N outputs corresponding to N-given angular positions of foot pedal.

Connected to the opposite end region of pedal shaft 50, also along shaft axis 60, are motor means 70, which preferably comprise a stepper motor of a known type. Motor means 70 are importantly connected for driving pedal shaft 50 in a counterclockwise or "return" direction (see Arrow C) when the motor means are energized (as described below) at one or more preselected (given) pedal angular positions relative to the zero reference position, according to the particular function or functions to be performed by implement 18.

At pedal rotational positions at which motor means 70 are energized, an operator is required to apply additional foot pressure on pedal 54 to overcome the driving torque on shaft 50 provided by motor means, the increased foot pressure required to depress foot pedal 54 serving to alert the operator that some preestablished or given event, such as the switching from one operational function to another, will occur if the foot pedal is depressed further.

As is described below, motor means 70 can be programmed to be energized at any desired angular position of foot pedal 54, and the angular foot pedal positions at which motor means 70 is energized may be different for different functions to be controlled by foot pedal control system 14.

An ophthalmic surgeon performing phacoemulsion surgery ordinarily employs the following sequence of operations or functions:
  i) irrigation of the eye with a saline solution;
  ii) a combination of simultaneous irrigation and aspiration of the irrigating fluid; and
  iii) a combination of fluid irrigation of the patient's eye, the ultrasonic emulsification of the eye lens, and the aspiration of the irrigation fluid and broken up particles of the lens.

During this process, the surgeon may, however, want the option of switching back to just fluid irrigation and fluid aspiration without lens emulsification. These functions are referred to as modes and are selected at the front panel of console 16 and are directed to foot pedal processor 40 by mode selector 22.

The present invention provides the kind of control required of the foot pedal control system 14 in order to provide the functional operation of hand-held implement 18, for each of the possible modes. Accordingly, it is required of logic means to provide the necessary functional control signals to console 16 (over a conduit or group of conduits 74) so that, for example, at a certain predetermined (and convenient) angular position of foot pedal 54, a signal is provided by logic means 40 "directing" console 16 to provide a flow of irrigating fluid to implement 18, and at another predetermined, angular position of the foot pedal to provide emulsifying ultrasonic energy to the implement.

It is, of course, to be understood that the control provided by foot pedal control system 14 to implement 18, through console 16, should be repeatable. That is, certain specific control signals should be provided by foot pedal control system 14 whenever foot pedal 54 is at a specific angular position, and the same sequence of signals should be provided at the same position whenever the foot pedal is depressed.

The function of foot pedal shaft position indicator or encoder 62 and counter 32 is to precisely, accurately, and repeatably provide to logic means 40 digital output signals which correspond to and are representative of the angular position of foot pedal 54 relative to its zero (undepressed) position. Encoder 62 provides signals which are decoded by counter 32 into increment or decrement events. In this manner, counter 32 provides a numerical representation of the angular position of foot pedal 54, such representation being used by processor 40 as a pointer into digital storage means 34.

Based upon "learning" from pedal shaft position indicator 62 the exact angular position of foot pedal 54, it is a function of logic means 40 to provide to console 16 the requisite control signals associated with that foot pedal position. Another function of logic means 40 is to provide energizing signals to motor means 70, over a conduit 76, whenever pedal shaft indicator means 62 signals the logic means that pedal 54 is at a predetermined angular position at which the energizing of motor means is required to provide pedal back pressure.

Accordingly, memory means 34 is configured for storing whatever predetermined sets of control signs are needed to be provided to console 16 as foot pedal 54 is depressed from its zero (at rest) position to its fully depressed position.

Preferably, memory means 34 are configured for storing N sets of given control signals to be provided to console 16 for N corresponding angular positions of foot pedal 54 (that is, of pedal shaft 50) as detected or determined by position indicator 62 and counter 32. Generally, among some of the N sets of given control signals stored in storage means 34 are one or more control signals causing the energizing of motor means 70 at given pedal shaft angular positions.

Memory means 34 may advantageously be in the form of an address card 77 having N addresses, and in which, each address corresponds to a particular one of the N angular positions of foot pedal 54 (that is, of pedal shaft 50). In each of the N address positions of address card 77, there is stored the set of digital output control signals required for the corresponding pedal shaft position. Processor 36 functions to decode the signals from shaft angular position indicator 62 and, in conjunction with counter 34, provides a corresponding address "pointer" into address card 77.

Thus, when foot pedal 54 is depressed by an operator, position indicator 62 provides a series of output signals which are counted by counter 32 to produce data related to the angles through which pedal shaft 50 is rotated. These output signals are provided over a conduit 78 to counter 32 which, responsive thereto, provides digital counts over a conduit 80 to processor 36.

Responsive thereto, processor 36 provides a corresponding sequence of address "pointers" over a conduit 82 to memory means 34 (that is, to address card 77), each of these address pointers corresponding to a particular angular position of pedal shaft 50, as determined by position indicator 62. Whenever an address pointer is received by storage means 34, the set of control signals in the address "pointed" to is outputted over conduit 74 to console 16, wherein the control signals are used to control functions of apparatus 12 in a given manner.

In addition to providing particular output control signals to console 16, storage means 34 preferably provides particular digital output signals (according to the accessed addresses in the storage means) over a conduit 86 to digital-to-analog (D/A) converter 38. A corresponding analog signal is provided from D/A converter 38 over a conduit 88 to console 16 for the operation of variable controls in apparatus 12, such as emulsification power which is responsive to an analog voltage signal.

A reset switch 90, preferably of the optical type, is mounted adjacent to foot pedal 54 and is connected to processor 36 and counter 32 (through amplifier 64) by a conduit 92 for resetting the processor when the foot pedal is at its zero position. This resets counter 32 when pedal 54 is at the zero position.

The use of a plurality of similar address cards 77 to comprise storage means 34 is advantageous, since each address card can be provided with N sets of given sets of output control signals (corresponding to N different addresses and N given foot pedal angular positions) appropriate for a particular function (or group of functions) which apparatus 12 is required to perform through hand-held implement 18. The appropriate address card 77 is selected, through processor 36, by function selector 22 on console 16 when a given function (or group of functions) of the apparatus is selected.

For example, in the case of a phacoemulsifier, one function is irrigation only, another is irrigation and aspiration and emulsification, another is phacoemulsification and still another is cautery. Once a particular function (or group of functions) is selected by selector 22, the corresponding address card 77 in storage means 34 is concurrently selected so that as address pointers are generated in processor 36 (as above-described), the address pointers are directed to the selected address card whose N sets of output control signs are appropriate for the selected function.

As a consequence, the selection of a particular address card 77 in storage means 34 in effect reprograms the control provided by foot pedal 54. That is, the full travel of foot pedal provides N particular sets of given out control signals to console 16 when one address card 77 is selected; and another, different set of control signals to the console when another address card is selected; still another N set of output control signals when still another address card is selected; and so on.

By way of illustrative example, this reprogramming of foot pedal 54 is depicted for a phacoemulsifier in the following Table, which shows the different operations enabled by the foot pedal as a function of foot pedal travel. Although, as shown in the Table, functions within operations switch at the same pedal positions for all the operations, it is to be understood that, if desired, address cards 77 can be programmed so that there is no such uniformity.

| Function | FOOT SWITCH POSITION | | | |
|---|---|---|---|---|
| | a | b | c | d |
| Irrigation/ Aspiration | No Function | Irrigation | Irrigation/ Aspiration | Irrigation/ Aspiration |
| Phacoemul- sion | No Function | Irrigation | Irrigation/ Aspiration | Irrigation/ Aspiration/ Emulsification |
| Phacoemulsi- fication | No Function | Irrigation | Irrigation/ Aspiration/ | Irrigation Aspiration/ |

-continued

| Function | FOOT SWITCH POSITION | | | |
|---|---|---|---|---|
| | a | b | c | d |
| Wet Field Cautery (Voltage) | No Function | Cautery | Cutting Cautery | Cutting Cautery |

For purposes of better illustrating the present invention relating to foot pedal control system 14, counter 32, digital storage means 34, processor 36, and D/A converter 38 are shown and described above as being separate from one another and from apparatus 12, as may sometimes be advantageous.

However, it is to be appreciated that such is not necessarily the case and that counter 32, storage means 34, processor 36, and/or D/A converter may alternatively be integrated together and/or may alternatively be fully integrated into apparatus 12, for example, into console 16.

It is also to be appreciated that amplifier 64, although shown on the drawing as being separate from foot pedal assembly 30, may advantageously be integrated thereinto so as to form a convenient, compact unit. The purpose of amplifier 64 is to enable conduits 78 and 92 to be of substantial length with the majority of components being remote from foot pedal assembly 30.

Moreover, although conduits 76, 78 and 92 are depicted in the drawing as being separate conduits, it will be appreciated that, in practice, such conduits would be bundled together in a single cable assembly connected to foot pedal assembly 30.

Conventional use of the hereinabove referenced apparatus provides for three foot pedal operational ranges hereinabove identified. Traditionally, these three ranges were established with equal amounts of travel or foot pedal arc. Specifically, the total amount of foot pedal arc of 15° was equally divided by equal amounts of 5° or travel for each of the three modes.

In accordance with the method of the present invention, an angular range of foot pedal operation is established for each of the modes of operation, namely, irrigation of an eye with a saline solution; simultaneous irrigation and aspiration of fluid; and simultaneous irrigation, emulsification of tissue, and aspiration of same. Angular ranges are established as being consecutive and in combination defining a total angular displacement, with the foot pedal preferably about 15°.

In utilizing the hereinabove-described system 14, a linear relationship between the angular position of the foot pedal within each range and an output signal from the foot pedal within each range is assigned.

Importantly, the foot pedal control sensitivity is determined, or adjusted, by changing the range of position of foot pedal within each of the selected modes.

That is, the foot pedal angular range for the irrigation mode may be established at 2°, and the foot pedal angular range for the simultaneous irrigation and aspiration of fluid may be set at about 5° with the foot pedal angular range for simultaneous irrigation, emulsification and aspiration being set for about 8°.

By assigning a greater range, namely 8°, to the angular range available for simultaneous irrigation, emulsification and aspiration mode, the user is provided with a more gradual and linear operation within the range. This is important from a control standpoint because it enables a more gradual change of operation within a mode which may be suitable for beginning users of the equipment or for personal preference of a user.

Thus, as hereinabove set forth, the range of motion usable in the simultaneous irrigation, emulsification, and aspiration is 60% greater when the range is set at 8° as opposed to 5°. Thus, the change of fluid flow during irrigation, emulsification and aspiration may be more gradually changed, which is not only suitable for draining purposes but also may be preferred by a physician user, depending upon circumstances of the operation.

Alternatively, as an important aspect of the present invention, the foot pedal angular range for the irrigation mode may be set to about 2°; the foot pedal angular range for the simultaneous irrigation and aspiration of fluid may be set at about 8°; and the foot pedal angular range for simultaneous irrigation, emulsification and aspiration may be set at about 5°.

This configuration allows a greater degree of sensitivity in the 8° range established for the simultaneous irrigation and aspiration of fluid. Such an increase to sensitivity may be preferred when irrigation and aspiration are performed within the eye, proximate critical areas such as the retina.

Although there has been hereinabove described a method for operating phacoemulsifier apparatus in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. In the performance of phacoemulsification, a method for operating phacoemulsifier apparatus, said phacoemulsification requiring at least three modes of operation of said phacoemulsifier apparatus, including: irrigation of an eye with a saline solution; simultaneous irrigation and aspiration of fluid; and simultaneous irrigation, emulsification of tissue and aspiration of same, said phacoemulsifier apparatus having a foot control for controlling the modes of operation, said method comprising the steps of:

establishing an angular range of foot pedal operation for each of the modes of operation, said angular ranges being consecutive and, in combination, defining a total angular displacement for said foot pedal;

assigning a linear relationship between the angular position of the foot pedal within each range and an output signal from the foot pedal within each range; and adjusting foot pedal control sensitivity by changing the range of position of the foot pedal for selected modes of operation.

2. The method according to claim 1, wherein the total angular displacement for said foot pedal is established at 15 degrees; the foot pedal angular range for the irrigation mode is set at about 2 degrees; the foot pedal angular range for simultaneous irrigation and aspiration of fluid is set at about 5 degrees; and the foot pedal angular range for simultaneous irrigation, emulsification and aspiration is set at about 8 degrees.

3. The method according to claim 1, wherein the total angular displacement for said foot pedal is established at 15 degrees; the foot pedal angular range for the irrigation mode is set at about 2 degrees; the foot pedal angular range for simultaneous irrigation and aspiration of fluid is set at about 8 degrees; and the foot pedal angular range for simultaneous irrigation, emulsification and aspiration is set at about 5 degrees.

4. The method according to claim 1, wherein the total angular displacement for said foot pedal is established at 15 degrees and each of the foot pedal angular ranges for the three modes of operation is set to about 5 degrees.

* * * * *